United States Patent
Trammell et al.

(10) Patent No.: US 10,928,351 B2
(45) Date of Patent: Feb. 23, 2021

(54) PLASMA MODIFIED EPITAXIAL FABRICATED GRAPHENE ON SIC FOR ELECTROCHEMICAL TRACE DETECTION OF EXPLOSIVES

(71) Applicant: The Government of the United States of America, as represented by the Secretary of the Navy, Arlington, VA (US)

(72) Inventors: Scott A. Trammell, Springfield, VA (US); Rachael L. Myers-Ward, Springfield, VA (US); Sandra C. Hangarter, Gaithersburg, MD (US); Daniel Zabetakis, Brandywine, MD (US); David A. Stenger, Annapolis, MD (US); David Kurt Gaskill, Alexandria, VA (US); Scott G. Walton, Fairfax, VA (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 68 days.

(21) Appl. No.: 16/049,018

(22) Filed: Jul. 30, 2018

(65) Prior Publication Data
US 2019/0033247 A1 Jan. 31, 2019

Related U.S. Application Data

(60) Provisional application No. 62/538,433, filed on Jul. 28, 2017.

(51) Int. Cl.
*G01N 27/30* (2006.01)
*C30B 33/04* (2006.01)
(Continued)

(52) U.S. Cl.
CPC .............. *G01N 27/308* (2013.01); *C30B 1/02* (2013.01); *C30B 29/02* (2013.01); *C30B 33/04* (2013.01); *G01N 33/22* (2013.01); *G01N 27/48* (2013.01)

(58) Field of Classification Search
CPC ...... G01N 27/308; G01N 33/22; G01N 27/48; G01N 27/301; G01N 27/28;
(Continued)

(56) References Cited

U.S. PATENT DOCUMENTS

| | | | |
|---|---|---|---|
| 2014/0367277 A1* | 12/2014 | Crawford | G01N 27/28 205/786.5 |
| 2018/0052134 A1* | 2/2018 | Kawde | C25D 9/08 |
| 2018/0175213 A1* | 6/2018 | Colinge | H01L 29/1606 |

OTHER PUBLICATIONS

Trammell et al "Plasma-Modified, epitaxial Fabricated Graphene on SiC for the Electrochemical Detection of TNT", Sensors, 2016, 16, 1281 (Year: 2016).*

* cited by examiner

*Primary Examiner* — Xiuyu Tai
(74) *Attorney, Agent, or Firm* — US Naval Research Laboratory; Richard Bis

(57) ABSTRACT

An electrochemical cell includes a working electrode in contact with an aqueous electrolyte solution, a counter electrode in contact with the aqueous electrolyte solution, and a reference electrode in contact with the aqueous electrolyte solution. The working electrode comprises a plasma modified epitaxial synthesized graphene surface fabricated on SiC.

8 Claims, 3 Drawing Sheets

(51) Int. Cl.
    *C30B 29/02*     (2006.01)
    *C30B 1/02*     (2006.01)
    *G01N 33/22*     (2006.01)
    *G01N 27/48*     (2006.01)

(58) Field of Classification Search
    CPC .... G01N 33/1886; G01N 27/302; C30B 1/02;
              C30B 29/02; C30B 33/04; C25D 9/08;
                                E21B 47/00
    See application file for complete search history.

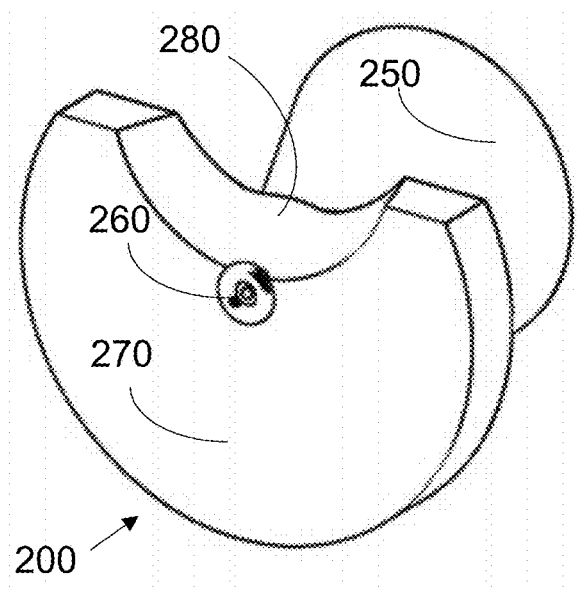 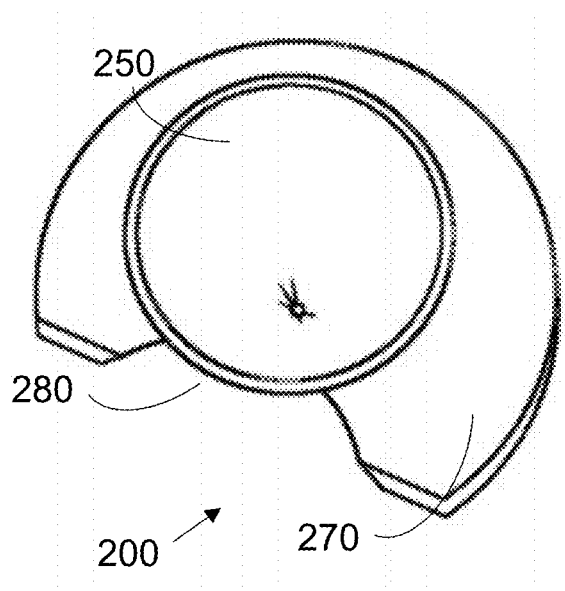
FIG.2  FIG. 3

PLASMA MODIFIED EPITAXIAL FABRICATED GRAPHENE ON SIC FOR ELECTROCHEMICAL TRACE DETECTION OF EXPLOSIVES

RELATED APPLICATIONS

This application claims the benefit of U.S. Provisional Application No. 62/538,433 filed Jul. 28, 2017, which is hereby incorporated herein by reference.

FIELD OF INVENTION

The present invention relates generally to electrochemical detection of TNT, and more particularly to plasma-modified, epitaxial fabricated graphene on SiC for such detection.

BACKGROUND

Graphene is an excellent sensor material because it is composed entirely of surface atoms, with exceptional physicochemical properties including high specific surface area, high carrier mobilities, and extremely low noise characteristics. Being all surface, the electronic properties of graphene show a strong dependence on surface adsorbates that can alter the charge carrier concentration of graphene, leading to measurable changes in conductivity. Furthermore, chemically modified graphene has been demonstrated to have shifts in its chemical reactivity making graphene an attractive material for use in electroanalytical techniques since it offers a wide electrochemical potential window.

For nitroaromatic electrochemical detection, a variety of preparation methods utilizing graphene or reduced graphene-oxide as a working electrochemical sensor have been reported with limits of detection (LOD) for 2,4,6-trinitrotoluene (TNT) ranging from 0.2 ppb to 100 ppb. Compared to other forms of carbon, e.g. glassy carbon (LOD=130 ppb) or screen printed carbon (LOD=200 ppb), graphene-based sensors regularly require an electrochemical accumulation step where an applied voltage at the working electrode is used to accumulate TNT at the surface of the electrode, a preconcentration step which utilizes large volume samples to provide sufficient analyte mass for obtaining a detectable signal, or an amplification step in which the TNT signal is enhanced using an electrochemical technique termed redox cycling, all to improve the electrochemical response. In addition, the preparation methods of the working electrode are often limited in scalability making practical application on the industrial scale nearly intractable.

SUMMARY OF INVENTION

Herein described is an apparatus and a method of manufacturing the same that show plasma modified epitaxial synthesized graphene on SiC having improved electrochemical detection of TNT (LOD~20 ppb) without the need for an accumulation step, a preconcentration step which utilizes large volume samples to provide sufficient analyte mass for obtaining a detectable signal, or an amplification step in which the TNT signal is enhanced using an electrochemical technique termed redox cycling.

Also described herein are miniaturized, low-power electrochemical sensors for the detection and identification of explosives as well as their precursors and degradation products in the environment. The electrochemical reduction of nitro-aromatics is a convenient detection method for common explosives such as TNT. Devices in accordance with the present invention show a profound increase in the detection of TNT using plasma modified graphene on a SiC surface. The graphene surface was chemically modified using electron beam generated plasmas. The use of this chemical modification route enabled enhancement of the electrochemical signal for TNT. In addition, the synthesis approach is a high-throughput, high-volume process amenable to industrial applications. High quality epitaxial graphene (EG) is easily grown over large area SiC substrates, while plasma processing is a rapid approach to large area substrate processing, which utilizes little waste volume. This combination facilitates low cost, mass production of sensors.

According to one aspect of the invention, an electrochemical cell includes a working electrode in contact with an aqueous electrolyte solution; a counter electrode in contact with the aqueous electrolyte solution; and a reference electrode in contact with the aqueous electrolyte solution. The working electrode comprises a plasma modified epitaxial synthesized graphene surface fabricated on SiC.

Optionally, the graphene surface is approximately 1.6 $mm^2$.

Optionally, the electrochemical cell includes a cell on top of the working electrode comprising an open-ended container and a gasket disposed between the container and the working electrode and configured to prevent leaks therebetween.

Optionally, the electrochemical cell includes a base extending laterally outward from the electrodes below the cell and configured for clamping, the broad base having a cut-out allowing access to the working electrode, and wherein the reference and counter electrodes are suspended in an upper funnel-shaped well which also holds the electrolyte.

Optionally, the working electrode is a single layer, non-flaky detection element.

Optionally, the working electrode comprises a surface atomic percentage of oxygen, as measured by X-ray photoelectron spectroscopy, of 10-15% $O_2$.

Optionally, the working electrode comprises a surface atomic percentage of oxygen, as measured by X-ray photoelectron spectroscopy, of 11.7% $O_2$.

Optionally, thickness of the epitaxial graphene layers may be ≈1-2 monolayers.

According to another aspect of the invention, a method of fabricating an electrochemical sensor having epitaxial graphene on SiC, includes the steps of: preparing a SiC surface for epitaxial graphene growth by in-situ $H_2$ etching, thereby forming bilayer stepped morphology and removing any polishing scratches created during the manufacturing of the SiC substrate; sublimating Si from semi-insulating, Si-face, on-axis, 6H-silicon carbide (SiC) substrates in a chemical vapor deposition reactor; cooling the epitaxial graphene on SiC; evacuating the reactor; and chemically modifying the epitaxial graphene using electron-beam generated plasmas to introduce and control relative concentration of functional groups on the graphene surface.

Optionally, the step of chemically modifying the epitaxial graphene includes the steps of: producing pulsed high-energy electron beams by driving a linear hollow cathode with a −2 kV square wave for a duration of 1 ms at a duty factor of 10%; and passing the beams through a slot in a ground anode and terminating the beams at a second grounded anode located further downstream of the beam. The slotted anode defines a cross section of the beams, and volume between the two anodes defines a processing region.

Optionally, the electron beams are magnetically confined to minimize spreading via collisions with background gas, producing a sheet-like plasma in the processing region.

Optionally, the method includes placing graphene substrates on a processing stage located approximately 2.5 cm from the electron-beam axis; and after evacuating the processing reactor to base pressure, introducing reactive gases.

Optionally, the reactive gasses are one of $O_2$ or $N_2$.

Optionally, operating pressures may be varied from approximately 25 to 90 mTorr in order to vary functional group density on the surface of epitaxial graphene.

Optionally, the step of sublimating takes place at a temperature of approximately 1540° C. and a pressure of approximately 100 mbar.

Optionally, the step of sublimating includes suppressing the sublimation of Si in order to control the thickness of the epitaxial graphene layers using ambient Ar.

Optionally, the step of cooling is conducted in Ar to a temperature 800° C.

The foregoing and other features of the invention are hereinafter described in greater detail with reference to the accompanying drawings.

BRIEF DESCRIPTION OF THE DRAWINGS

FIG. 2 shows a figure of an exemplary electrochemical cell;

FIG. 3 shows a figure of an exemplary electrochemical cell;

DETAILED DESCRIPTION

Figure 1:
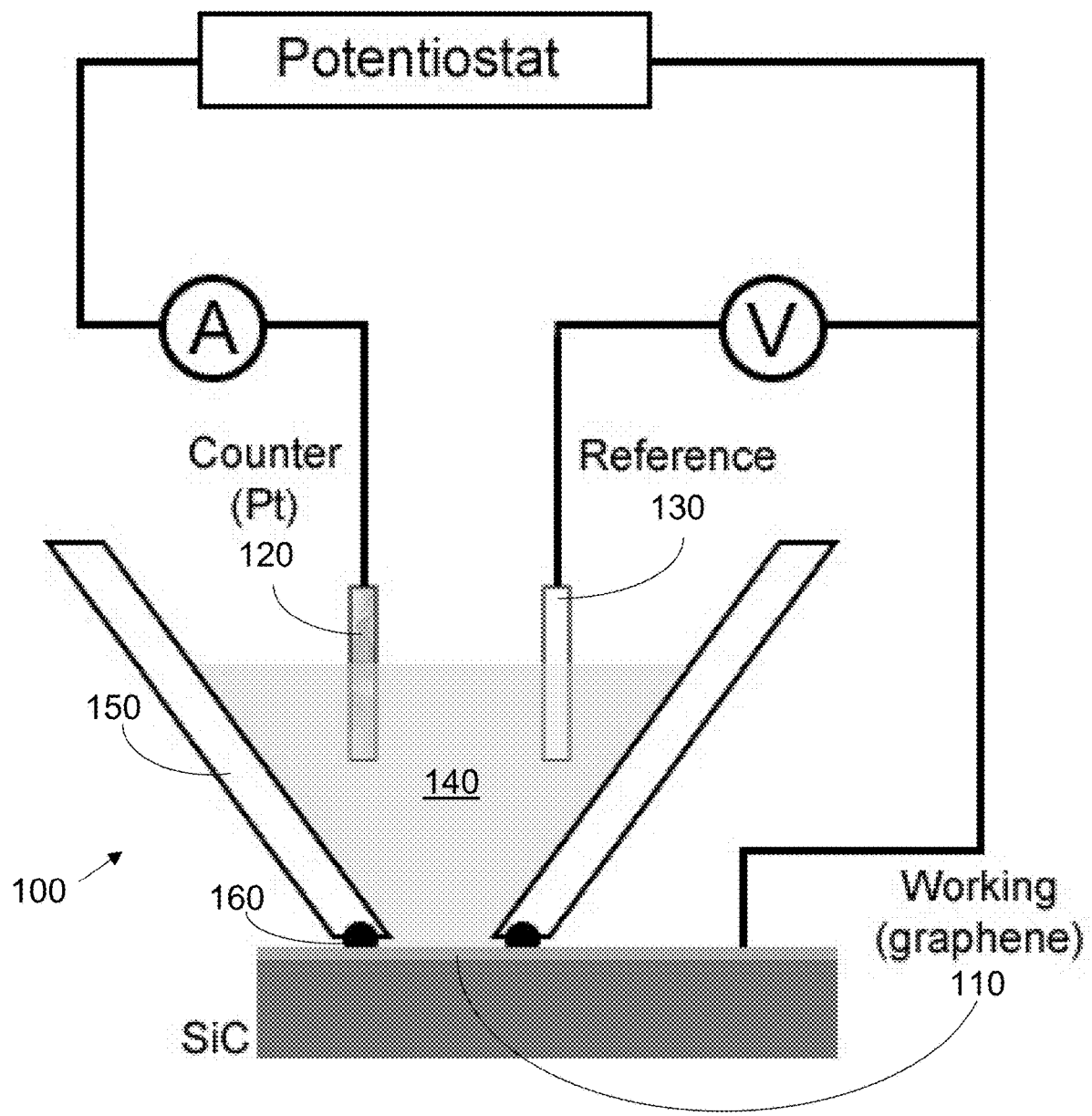
FIG. 1 shows a schematic representation of an exemplary electrochemical cell.

Epitaxial graphene may be synthesized by means of Si sublimation from semi-insulating (SI), Si-face, on-axis, 6H-silicon carbide (SiC) substrates. The growth may take place in a chemical vapor deposition reactor at a temperature of, for example, 1540° C. and a pressure of, for example, 100 mbar using Ar ambient. The argon may be used to suppress the sublimation of Si in order to control the thickness of the epitaxial graphene layers. Prior to growth, the substrate may be in-situ $H_2$ etched to prepare the SiC surface for epitaxial graphene growth, by forming bilayer stepped morphology and removing any polishing scratches created during the manufacturing of the SiC substrate. After growth, the sample may be cooled in Ar to 800° C., at which point the reaction tube may be evacuated. The thickness of the epitaxial graphene layers may be, for example, $\approx$1-2 monolayers and may be determined by X-ray photoelectron spectroscopy (XPS) or Raman spectroscopy.

The epitaxial graphene may be chemically modified using electron-beam generated plasmas, which are well-suited for large area plasma processing of atomically thin materials. The processing system and protocols followed introduce and control the relative concentration functional groups on the surface of graphene. Briefly, pulsed high-energy electron beams may be produced by driving a linear hollow cathode with a −2 kV square wave for a duration of 1 ms at a duty factor of 10%. The emergent beam passes through a slot (1×20 cm$^2$) in a ground anode, and terminates at a second grounded anode located further downstream (50 cm). The slotted anode defines the beam cross section and the volume between these two anodes defines the processing region. The electron beam may be magnetically confined, to minimize spreading via collisions with the background gas, producing a sheet-like plasma in the processing region. Substrates (graphene) may be placed on a processing stage located, for example, 2.5 cm from the electron-beam axis. After evacuating the processing reactor to base pressure ($\sim$1×10$^{-6}$ Torr), reactive gases may be introduced at, for example, 5% of the total flow rate with argon providing the balance to achieve a target operating pressure. The reactive gases used are either $O_2$ or $N_2$, depending on the desired functionalities. To vary the functional group density on the surface of epitaxial graphene, operating pressures may be varied from 25 to 90 mTorr by controlling the total flow rate (50 to 180 sccm). The total processing time may be approximately 60 seconds.

Ex-situ surface diagnostics may be performed before and immediately after plasma processing to determine the starting material quality and chemistry and the changes resulting from plasma modification. Chemical changes and the resulting bonding characteristics in the graphene due to plasma processing may be tracked by X-ray photoelectron spectroscopy (XPS) using, for example, a Thermo Scientific K-Alpha spectrometer with a monochromatic Al—K alpha source with a spot size of 400 μm. Chemical analysis may be performed using software such as, for example, Avantage and Unifit softwares.

Electrochemical measurements may be performed using, for example, a potentiostat model #660 from CH Instruments. As shown in FIG. 1, an electrochemical cell 100 may be composed of three electrodes (working 110, counter 120, and reference 130) all immersed in (or in contact with) an aqueous electrolyte solution 140. The working electrode 110—as received or chemically-modified epitaxial graphene—may be approximately 1.6 mm$^2$. Since the current signal generated in electrochemical measurements is proportional to the area of the working electrode, it may be advantageous to restrict the active electrode to a well-defined area. When working electrodes are manufactured from rigid substrates it is practical to form a cell on top of the electrode using an open-ended container 150 and a gasket 160 to prevent leaks.

In order to form such a cell and to allow for the electrical connection to the graphene/SiC substrate, a custom cell 200 shown in FIGS. 2 and 3 may be designed for use. Such a cell may contain an integrated gasket on the container 250, a broad base for clamping 270, and a cut-out 280 to allow maximum access to the working electrode. The reference and counter electrodes may be suspended in the upper funnel-shaped well which also holds the electrolyte.

Electron beam generated plasmas produced in $O_2$/Ar mixtures result in the introduction of oxygen functionalities on the surface of graphene with the relative concentration increasing with increasing operating pressure. Chemical changes and the resulting bonding characteristics in the graphene due to plasma processing may be tracked by XPS. Following plasma exposures, the presence of oxygen is clear (O1s) and show a gradual increase in the total oxygen content with increasing operating pressure, going from 3.6% at 50 mTorr to 11.7% at 90 mTorr. A better understanding of the functionalization can be developed by comparing the high-resolution spectra of graphene before and after processing for each plasma processing condition. Additionally, C1s spectra shows the incorporation of oxygen functionalities which are assigned to carbon bonding involving ethers or alcohols (C—O—C, C—O, or C—OH) and carbonyl bonds (=O) located at $\approx$286.4 eV and $\approx$287.1 eV, respectively. Before plasma processing, the O1s scans show little to no signal, indicating no oxygen present on the samples. After plasma processing, features on the O1s spectra arise at three different locations corresponding to (Si—O) bonding at ≈534.3 eV, ethers or alcohols (C—O—C, C—O, or C—OH) at ≈533.3 eV and carbonyl groups (C═O) at ≈532.2 eV. The de-convoluted O1s spectra shows pressure dependence in terms of the amount and type of carbon-oxygen bonds formed in the $O_2$/Ar plasma.

Similarly, nitrogen functionalities can be introduced in a controlled manner using electron beam generated plasmas produced in an $N_2$/Ar mixture at various operating pressures. The assignments of the C1s components are challenging due to the overlapping binding energies of nitrogen and oxygen species with those of the interfacial layer. However based on the combined features of the C1s and N1s high resolution spectra, the identifiable peaks are located at ≈283.6 eV, 284.5 eV, 285.3 eV, are attributed to the Si—C, C—C $sp^2$, and interfacial layer, respectively. The peaks located at higher binding energies (>286 eV) are attributed to nitrogen and oxygen functionalities. Notably C—N and C—O at ≈286.1 eV, C═N at ≈287.4 eV, C═O and N—C═O at ≈288.3 eV, and O—C═O at ≈289.4 eV. The N1s spectra indicate that nitrogen functionalities are present primarily in the amide and pyrolic configurations.

The electrochemical response of TNT reduction at the graphene working electrode may be characterized using square-wave voltammetry, which is a common electroanalytical technique for analytical applications since it diminishes non-faradic charging currents that develop at the solution electrode interface when employing potential sweeping techniques. In square wave voltammetry, a potential staircase is overlaid on the voltage ramp as the voltage is swept in the desired range at the working electrode. The reduction (or oxidation) of the analyte is then measured as the voltage approaches its formal redox potential. The current is then measured at different points of the potential waveform to minimize capacitive charging at the solution electrode interface. Since non-faradic current decays faster than faradic current, a square wave voltammogram can be generated by taking the difference of current between the points subtracting out the capacitive charging current making the detection limits typically better then cyclic voltammetry.

To record the square wave voltammograms, the modified graphene samples may be mounted in an electrochemical cell and background measurements may be recorded before the addition of TNT.

The square wave voltammograms were measured in air-saturated phosphate buffered saline (PBS, pH 7.4) solutions from 0 to −1.0 V vs. Ag/AgCl reference electrode. With unmodified graphene, the 1$^{st}$ reduction of TNT ($E_{pc}$=−0.8 vs Ag/AgCl) is shifted to significantly more negative voltages compared to oxygen functionalized graphene ($E_{pc}$=−0.58 V vs. Ag/AgCl) and nitrogen functionalized graphene ($E_{pc}$=−0.5 V vs. Ag/AgCl). In square wave voltammetry, the peak position of the maximum absolute value of measured current is a reflection of both thermodynamic and kinetic properties of the electrochemical system; other carbon electrodes such as glassy carbon shows the 1st reduction near −0.5 V vs. Ag/AgCl. Moreover, the amplitude of the peak using the oxygen functionalized graphene working electrode shows a significant increase $E_{pc}$ compared to untreated and nitrogen-functionalized graphene signal. This result indicates either an increase in the active surface area of the graphene or an increase in the rate of reduction of the TNT or both. For nitrogenated graphene, there is little change to the net amplitude of the signal, however, the peak potential shifts more positive with increasing nitrogen surface coverage, and begins to saturate at 13 atomic %. For the oxygenated graphene, the shift in peak potential saturates near 4 atomic %. However, at 11.7 atomic %, the net amplitude of the signal of TNT is significantly enhanced by 10 fold compared to unmodified graphene.

The significant enhancement in signal amplitude of oxygen-functionalized epitaxial graphene allows analysis of the trace detection of TNT in PBS. Example results show a large dynamic range with signal vs TNT concentration between 150 to 5000 ppb and a smaller range with a larger sensitivity between 40 to 150 ppb. The data can be fit to a two-site Langmuir isotherm (eq. 1) suggesting different active sites with different TNT affinities on the graphene surface.

$$A = a((K_a[\text{TNT}])/(1+(K[\text{TNT}])) + b((K_b[\text{TNT}])/(1+(K_b[\text{TNT}])) \quad (1)$$

where A is net peak amplitude, a is the proportion of current due to the reduction of TNT at sites a, $K_a$ is the binding constant of TNT at sites a, b is the proportion of current due to the reduction of TNT at sites b, and $K_b$ is the binding constant of TNT at sites b. The sites with high affinities for TNT saturate with increasing TNT concentration, and the sites with lower affinities give rise to the large dynamic range. At 40 ppb (the lowest TNT concentration tested) the S/N ratio is 6. An estimated limit of detection=20 ppb is reasonable, based on the analytical standard S/N ratio of 3.

For carbon electrodes, surface preparation is often critical for the good electrochemical response of analytes. This has been shown when comparing basal plane to edge plane graphite, surface modification of glassy carbon, and more recently with different preparations of graphene and graphene oxides. A common theme to describe the phenomenon is that electron transfer between the analyte and carbon surface happens at defect sites, or chemical groups from the surface modification. In the present case, the initial graphene created on SiC gives a broad signal for TNT reduction at a more negative potential which suggests that graphene without any chemical modification has a slower electron transfer rate requiring a higher over potential to generate the TNT signal. Modification with oxygen and nitrogen both lower the over potential for the reduction of TNT. However, with oxygen modification a significant increase in signal amplitude as shown. In this case, a two-site Langmuir isotherms can fit the dose response curve and suggests that oxygen modification generates several sites on the graphene surfaces with different affinities of TNT.

An exemplary electrochemical cell is composed of three electrodes (working, counter, and reference) all immersed in (or in contact with) an aqueous electrolyte solution. In exemplary embodiments, the working electrode is the graphene surface fabricated on SiC and is approximately 1.6 $mm^2$. Since the current signal generated in electrochemical measurements is proportional to the area of the working electrode, it is advantageous to restrict the active electrode to a well-defined area. When working electrodes are manufactured from rigid substrates it is practical to form a cell on top of the electrode using an open-ended container and a gasket to prevent leaks. Allowing for the electrical connection to the graphene/SiC substrate, an exemplary cell is illustrated in FIGS. 2 and 3, introduced above. The cell contains an integrated gasket 260, a broad base 270 for clamping, and a cut-out 280 to allow maximum access to the working electrode. The reference and counter electrodes are suspended in the upper funnel-shaped well 250 which also holds the electrolyte.

Exemplary embodiments have shown an increase in the detection limit of TNT to 20 ppb using chemically-modified graphene on a SiC surface compared to untreated graphene.

The graphene surface was chemically modified using electron beam generated plasmas produced in oxygen- and nitrogen-containing backgrounds to introduce oxygen or nitrogen moieties. While both treatments enabled the enhancement of the electrochemical signal for TNT, oxygen-functionalized epitaxial graphene provided a more pronounced response. The synthesis approach is a high-throughput, high-volume process amenable to industrial applications. High-quality epitaxial graphene is easily grown over large area SiC substrates, while plasma processing is a rapid approach to large area substrate processing, which utilizes little waste volume. This combination may facilitate low cost, mass production of sensors.

Figure 4:
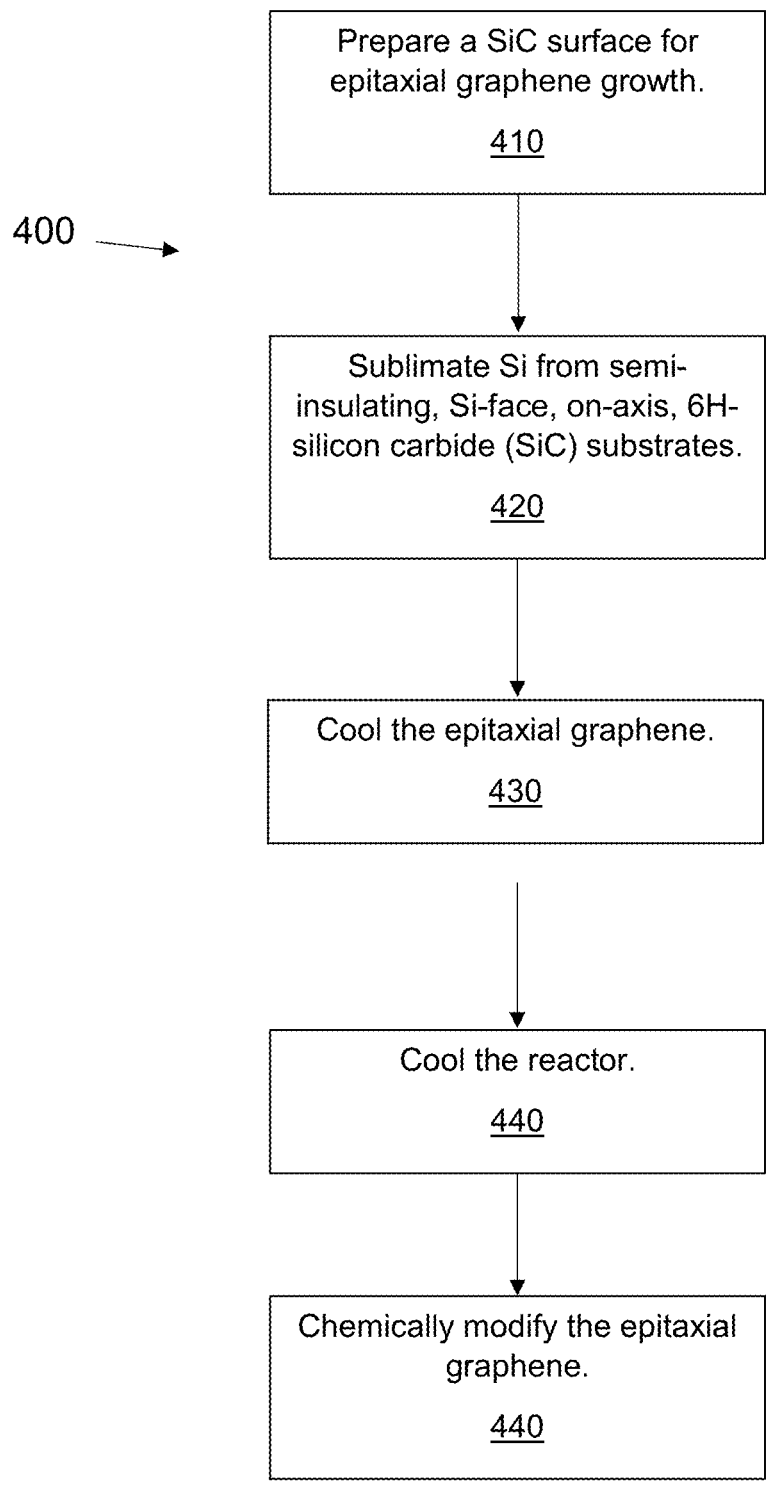
FIG. 4 shows a schematic of an exemplary method of manufacturing an exemplary electrochemical cell.

Shown schematically in FIG. 4, the method 400 for manufacturing a cell includes the following steps. At block 410, a SiC surface for epitaxial graphene growth is prepared by in-situ $H_2$ etching, thereby forming bilayer stepped morphology and removing any polishing scratches created during the manufacturing of the SiC substrate. At block 420, Si is sublimated from semi-insulating, Si-face, on-axis, 6H-silicon carbide (SiC) substrates in a chemical vapor deposition reactor. At block 430, the epitaxial graphene is cooled. At block 440, the reactor is cooled. At block 450, the epitaxial graphene is chemically modified using electron-beam generated plasmas to introduce and control relative concentration of functional groups on the graphene surface.

Block 450 may include the steps of producing pulsed high-energy electron beams by driving a linear hollow cathode with a −2 kV square wave for a duration of 1 ms at a duty factor of 10% and passing the beams through a slot in a ground anode and terminating the beams at a second grounded anode located further downstream of the beam. The slotted anode defines a cross section of the beams, and volume between the two anodes defines a processing region. The electron beams may be magnetically confined to minimize spreading via collisions with background gas, producing a sheet-like plasma in the processing region. Further, graphene substrates may be placed on a processing stage located approximately 2.5 cm from the electron-beam axis, and—after evacuating the processing reactor to base pressure—reactive gases may be introduced. These reactive gasses are preferably one of $O_2$ or $N_2$. Operating pressures may be varied from approximately 25 to 90 mTorr in order to vary functional group density on the surface of epitaxial graphene. At block 420, sublimating may take place at a temperature of approximately 1540° C. and a pressure of approximately 100 mbar. Further, the sublimation of Si may be suppressed in order to control the thickness of the epitaxial graphene layers using ambient Ar.

Scalable graphene growth over large surface areas is limited only by the substrate size. Currently, 150 mm SiC substrates are commercially available.

Epitaxial graphene is grown on semi insulating SiC and so, unlike chemical vapor deposition of graphene on copper, there is no need to transfer the graphene to a semi insulating substrate, thus facilitating the overall sensor fabrication.

Scaling of the electron beam generated plasma is straightforward. Exemplary systems are capable to a standard 200 mm wafer and reactors capable of 1 $m^2$ have been built.

The modified graphene is amenable to standard semiconductor processing methods, which are known to be economical, to create the explosives sensor. Assuming a die size of 1 $mm^2$, approximately 17,000 sensors could be produced from one 150 mm diameter wafer.

As an alternative embodiment, 4H—SiC can be used instead of 6H—SiC for the synthesis of epitaxial graphene.

Optionally, the number of epitaxial graphene layers may be modified to enhance the TNT detection (1-5 ML).

Further, growth on C-face instead of Si-face SiC may be used to increase epitaxial graphene thickness further.

Still further, graphene can be synthesized on various offcut substrates to obtain a beneficial signal response.

Optionally, detectors can be designed to be on a terrace with single thickness to reduce noise associated with thickness variability or oriented to reduce the effects of step bunching on signal response.

$H_2$ intercalation of the graphene may be conducted to eliminate the interfacial layer between the SiC and the graphene layer and improve signal response. Also, it is possible to optimize $O_2$ dose to improve TNT detection sensitivity. Moreover, distinct oxygen functional group types (epoxy vs hydroxyl vs carbonyl) can be introduced to improve interaction with nitro-aromatics to further decrease detection limits. The use of different gases (e.g. $NH_3$, $N_2+NH_3$) and/or mixtures (e.g. $O_2+H_2$) during plasma treatment to control the relative concentration of functional groups and/or introduce new functional groups to further increase detection limits.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. An electrochemical cell comprising:
   a working electrode in contact with an aqueous electrolyte solution;
   a counter electrode in contact with the aqueous electrolyte solution; and
   a reference electrode in contact with the aqueous electrolyte solution;
   wherein, the working electrode comprises a plasma modified epitaxial graphene surface synthesized from SiC.

2. The electrochemical cell of claim 1, wherein the graphene surface is approximately 1.6 $mm^2$.

3. The electrochemical cell of claim 1, further comprising a cell on top of the working electrode comprising an open-ended container and a gasket disposed between the container and the working electrode and configured to prevent leaks therebetween.

4. The electrochemical cell of claim 3, further comprising a base extending laterally outward from the electrodes below the cell and configured for clamping, the broad base having a cut-out allowing access to the working electrode, and wherein the reference and counter electrodes are suspended in an upper funnel-shaped well which also holds the electrolyte.

5. The electrochemical cell of claim 1, wherein the working electrode is a single layer, non-flaky detection element.

6. The electrochemical cell of claim 1, wherein the working electrode comprises a surface atomic percentage of oxygen, as measured by X-ray photoelectron spectroscopy, of 10-15% $O_2$.

7. The electrochemical cell of claim 6, wherein the working electrode comprises a surface atomic percentage of oxygen, as measured by X-ray photoelectron spectroscopy, of 11.7% $O_2$.

8. The electrochemical cell of claim 1, wherein thickness of the epitaxial graphene layers are in a range of 1 to 2 monolayers.

* * * * *